US011382553B2

(12) United States Patent
Han et al.

(10) Patent No.: US 11,382,553 B2
(45) Date of Patent: Jul. 12, 2022

(54) SYSTEM AND METHOD FOR DETECTING CONSISTENT CARDIAC ACTIVITY

(71) Applicant: ST. JUDE MEDICAL, CARDIOLOGY DIVISION, INC., St. Paul, MN (US)

(72) Inventors: Dongfeng Han, St. Paul, MN (US); Valtino X. Afonso, Oakdale, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 98 days.

(21) Appl. No.: 16/482,686

(22) PCT Filed: Jan. 25, 2018

(86) PCT No.: PCT/US2018/015242
§ 371 (c)(1),
(2) Date: Jul. 31, 2019

(87) PCT Pub. No.: WO2018/148026
PCT Pub. Date: Aug. 16, 2018

(65) Prior Publication Data
US 2019/0350477 A1 Nov. 21, 2019

Related U.S. Application Data

(60) Provisional application No. 62/457,018, filed on Feb. 9, 2017.

(51) Int. Cl.
*A61B 5/316* (2021.01)
*A61B 5/00* (2006.01)
(Continued)

(52) U.S. Cl.
CPC .............. *A61B 5/316* (2021.01); *A61B 5/349* (2021.01); *A61B 5/7264* (2013.01); *A61B 5/25* (2021.01)

(58) Field of Classification Search
CPC ....... A61B 5/316; A61B 5/349; A61B 5/7264; A61B 5/25; G16H 50/20
See application file for complete search history.

(56) References Cited

U.S. PATENT DOCUMENTS 6,301,496 B1 * 10/2001 Reisfeld .................. G06T 17/20
600/407
7,107,093 B2 * 9/2006 Burnes ................. A61N 1/3627
600/509

(Continued)

FOREIGN PATENT DOCUMENTS

WO 2015149153 A1 10/2015

OTHER PUBLICATIONS

International Search Report and Written Opinion for International Application No. PCT/US2018/015242, dated Apr. 9, 2018, 9 pages.

*Primary Examiner* — Gary Jackson
*Assistant Examiner* — Sebastian X Lukjan
(74) *Attorney, Agent, or Firm* — Armstrong Teasdale LLP

(57) ABSTRACT

The present disclosure provides systems and methods for detecting cardiac activations of a patient. A system includes a data acquisition system (DAQ) communicatively coupled to an activation detection module. The DAQ detects an electrogram generated at an electrode disposed on or in the patient. The activation detection module is configured to receive the electrogram from the DAQ and compute an activation response. The activation detection module is further configured to determine a set of candidate detection time points (CDTPs) in the activation response. The activation detection module is configured to compute respective deflection characteristics for each CDTP. The activation detection module is configured to identify a group of final detection time points (FDTPs) among the set of CDTPs for a metric corresponding to the respective deflection characteristics. The group of FDTPs has similar deflection char- (Continued)

acteristics. The activation detection module is configured to compute metrics based on the group of FDTPs.

20 Claims, 7 Drawing Sheets

(51) Int. Cl.
*A61B 5/349* (2021.01)
*A61B 5/25* (2021.01)

(56) References Cited

U.S. PATENT DOCUMENTS

| | | | | |
|---|---|---|---|---|
| 2009/0069704 | A1* | 3/2009 | MacAdam | G06T 7/0012 |
| | | | | 600/523 |
| 2012/0289845 | A1* | 11/2012 | Ghosh | A61B 5/686 |
| | | | | 600/510 |
| 2013/0006131 | A1* | 1/2013 | Narayan | A61B 5/4064 |
| | | | | 600/508 |
| 2015/0257671 | A1* | 9/2015 | Laughner | A61B 5/361 |
| | | | | 600/374 |

* cited by examiner

SYSTEM AND METHOD FOR DETECTING CONSISTENT CARDIAC ACTIVITY

CROSS REFERENCE TO RELATED APPLICATIONS

This application is the national stage entry of PCT/US2018/015242, filed on Jan. 25, 2018, which claims the benefit of priority to U.S. provisional application Ser. No. 62/457,018, filed Feb. 9, 2017, which are incorporated herein by reference in their entirety.

A. FIELD OF THE DISCLOSURE

The present disclosure relates generally to electrocardiography. In particular, in many embodiments, the present disclosure relates to systems and methods for detecting cardiac activations.

B. BACKGROUND OF THE DISCLOSURE

It is generally known, in physiology, that cells undergo periodic depolarization and repolarization that is essential to the functioning of and communication among those cells. Depolarization is a process by which a cell at resting potential, which is generally a negative internal charge and a relatively positive membrane charge, shifts such that the internal charge becomes more positive. Conversely, repolarization is a complimentary process by which the cell's charge shifts back toward resting potential.

During a cardiac cycle, cells of the atria first depolarize, causing contraction. The depolarization propagates over time, like a wave, arriving at cells of the ventricles as the atria finish contracting. Depolarization in the ventricles causes contraction, while the atria are repolarized and relaxed. The ventricles then repolarize and relax.

Electrocardiography is a technology by which cardiac electrical activity is monitored and recorded over time. Generally, the depolarization and repolarization patterns of the heart are detectable as small changes in charge in skin cells that are measured using, for example, various cutaneous electrodes. A graph of these charges, i.e., voltages, is referred to as an electrocardiogram (ECG). A typical ECG utilizes ten cutaneous electrodes placed in various locations on the limbs and chest. ECGs are often used to measure rate and rhythm of heartbeats, as well as to evaluate the cardiac cells to detect damage or diagnose potential heart conditions.

Additionally, in electrophysiological procedures, an array of electrodes located on a distal end of a cardiac catheter is placed on the cardiac muscle to produce an electrogram. Cardiac catheter electrodes generally include, for example, and without limitation, unipole and bipole electrodes. Bipole electrodes are self-referencing, measuring a potential across two contacts. Unipole electrodes are referenced to a common potential.

Each electrode of the ECG and electrogram produces ECG and electrogram traces. A fundamental aspect of the ECG and electrogram is the accurate detection of cardiac activations in each trace. Such detections are an ongoing challenge in creating useful products from an ECG, including, for example, and without limitation, a local activation time (LAT) map, a regular cycle length map, a voltage map, and a conduction velocity map. Such challenges are magnified when cardiac activations are more heterogeneous or transient, which can occur due to intermittent electrode-tissue contact or during atrial fibrillation, for example.

BRIEF SUMMARY OF THE DISCLOSURE

The present disclosure generally relates to electrocardiography and systems and methods for detecting cardiac activations. In many embodiments, the systems include an electrocardiogram system that provides accurate detection of cardiac activation times based on consistent deflection characteristics among multiple deflections in the electrogram. Embodiments of the systems and methods described herein utilize, for a given electrogram, a computed activation response to determine a set of candidate detection time points (CDTP). CDTPs can be determined using, for example, a dv/dt activation response, a wavelet transform activation response, an omnipolar activation response, or any other suitable means for computing an activation response for an electrogram. Embodiments of the systems and methods described herein then characterize each CDTP in the given electrogram by assigning deflection characteristics, such as, for example, cycle length, voltage, local signal-to-noise ratio (SNR), conduction velocity, and relative activation time. Embodiments of the systems and methods described herein then validate each CDTP based on the consistency of various deflection characteristics among groups of CDTPs. For example, CDTPs representing deflections having common deflection characteristics are grouped together, while CDTPs representing deflections that cannot be grouped are removed from consideration. The remaining CDTPs are referred to as final detection time points (FDTPs). Embodiments of the systems and methods described herein compute metrics based on the FDTPs. For example, a regular cycle length is computed from a group of FDTPs having the most consistent, i.e., regular, deflections or cardiac activations within a given observation window (OW). Similarly, for example, a conduction velocity (CV) is computed from a group of FDTPs having similar CV.

In one embodiment, the present disclosure provides a system for detecting cardiac activations of a patient. The system includes a data acquisition system and an activation detection module communicatively coupled thereto. The data acquisition system is configured to detect an electrogram generated at an electrode disposed on or in the patient. The activation detection module is configured to receive the electrogram from the data acquisition system and compute an activation response; to determine a set of candidate detection time points (CDTPs) in the activation response; to compute respective deflection characteristics for each CDTP; and to identify a group of final detection time points (FDTPs) among the set of CDTPs for a metric corresponding to the respective deflection characteristics. The group of FDTPs has similar deflection characteristics. The activation detection module is configured to compute the metric based on the group of FDTPs.

In another embodiment, the present disclosure is directed to a method of detecting cardiac activations. The method includes determining a set of candidate detection time points (CDTPs) for an electrogram; computing deflection characteristics for the set of CDTPs; grouping the set of CDTPs into groups of final detection time points (FDTPs) based on the deflection characteristics; and computing respective metrics for the groups of FDTPs.

The foregoing and other aspects, features, details, utilities and advantages of the present disclosure will be apparent from reading the following description and claims, and from reviewing the accompanying drawings.

BRIEF DESCRIPTION OF THE DRAWINGS

Corresponding reference characters indicate corresponding parts throughout the several views of the drawings. It is understood that that Figures are not necessarily to scale.

DETAILED DESCRIPTION OF THE DISCLOSURE

The present disclosure relates generally to electrocardiography. In particular, in many embodiments, the present disclosure relates to systems and methods for detecting cardiac activations for use in producing electrical activity maps and other diagnostic procedures. Such maps are generally produced from bipole electrograms that are dependent on direction of the cardiac wave-front relative to an orientation of the bipole electrode pair. It is further realized herein that such electrograms may include artifacts introduced by far-field cardiac electrical activity. For example, a unipole or bipole electrogram measured in the atria may have deflections due to cardiac activity occurring concurrently in the ventricles. More generally, a given electrogram may exhibit deflections for both local cardiac activation and nearby cardiac electrical activity.

Embodiments of the systems and methods described herein provide an electrocardiogram system that provides accurate detection of cardiac activation times based on consistent deflection characteristics among multiple deflections in the electrogram. Embodiments of the systems and methods described herein utilize, for a given electrogram, a computed activation response to determine a set of candidate detection time points (CDTP). CDTPs can be determined using, for example, a dv/dt activation response, a wavelet transform activation response, an omnipolar activation response, or any other suitable means for computing an activation response for an electrogram. Embodiments of the systems and methods described herein then characterize each CDTP in the given electrogram by assigning deflection characteristics, such as, for example, cycle length, voltage, local signal-to-noise ratio (SNR), conduction velocity, and relative activation time. Embodiments of the systems and methods described herein then validate each CDTP based on the consistency of various deflection characteristics among groups of CDTPs. For example, CDTPs representing deflections having common deflection characteristics are grouped together, while CDTPs representing deflections that cannot be grouped are removed from consideration. The remaining CDTPs are referred to as final detection time points (FDTPs). Embodiments of the systems and methods described herein compute metrics based on the FDTPs. For example, a regular cycle length is computed from a group of FDTPs having the most consistent, i.e., regular, deflections or cardiac activations within a given observation window (OW). Similarly, for example, a conduction velocity (CV) is computed from a group of FDTPs having similar CV.

Figure 1:
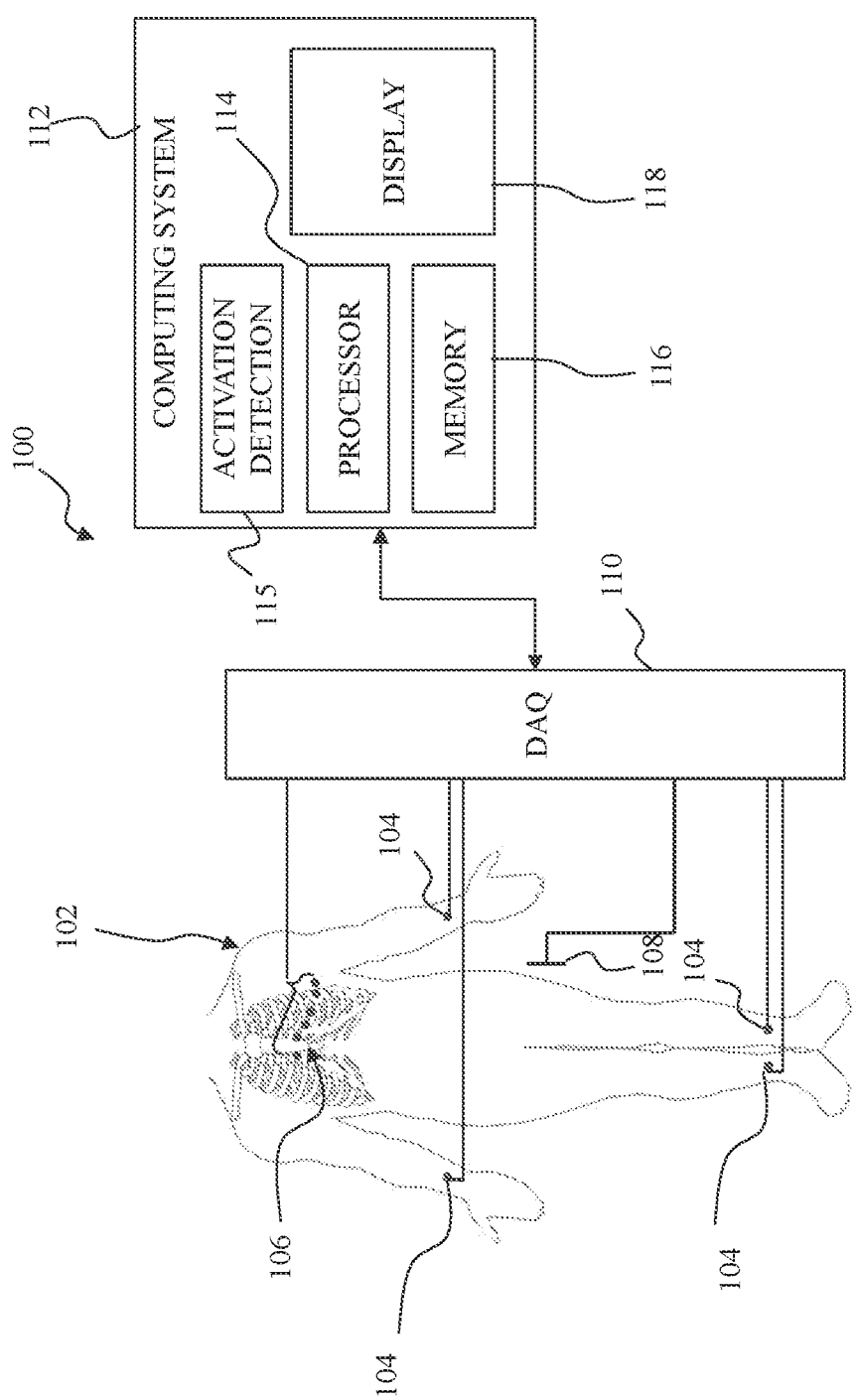
FIG. 1 is a schematic diagram of a system for conducting an electrocardiogram.

FIG. 1 is a schematic and block diagram of an ECG system 100 for conducting an ECG on a patient 102. ECG System 100 shown in FIG. 1 is sometimes referred to as a surface ECG that measures electrical activity of patient 102's heart using various cutaneous electrodes, including limb electrodes 104 and precordial electrodes 106. System 100, in certain embodiments may further include internal electrodes (not shown) inserted into patient 102 using a cardiac catheter. System 100 includes a common electrode 108 that, in certain embodiments, serves as a common reference for others of limb electrodes 104 and precordial electrodes 106, and, more specifically, any unipole electrodes among them.

Figure 2:
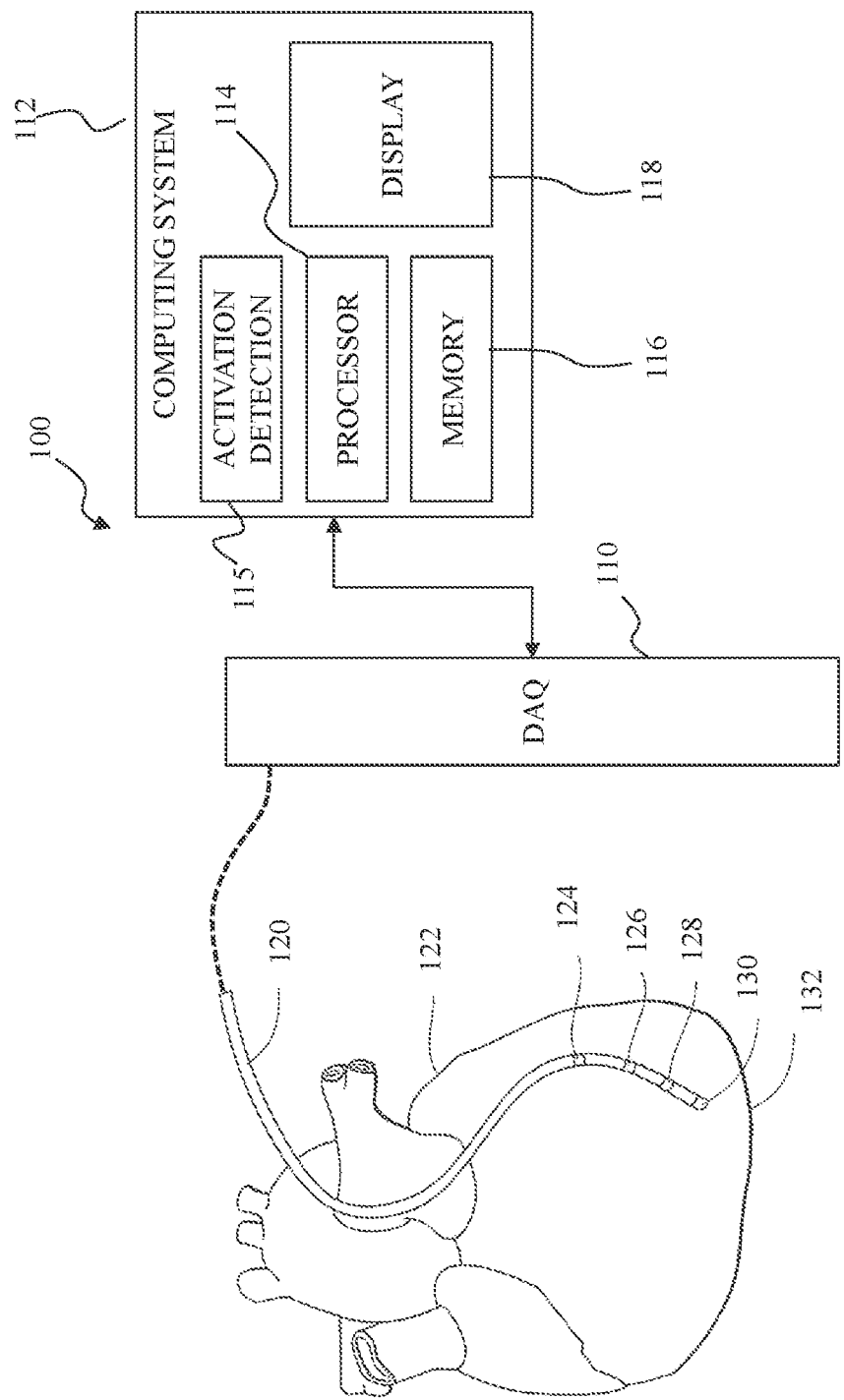
FIG. 2 is a schematic diagram of the system of FIG. 1 having a catheter.

FIG. 2 is another schematic and block diagram of ECG system 100, including a catheter 120 having various catheter electrodes 124, 126, 128, and 130, sometimes referred to as distal electrodes. Catheter 120, in certain embodiments, may utilize a single catheter having numerous splines, each with multiple electrodes. In alternative embodiments, system 100 may utilize multiple catheters 120, each with multiple electrodes. In certain embodiments, catheter 120 is embodied in a high-density grid catheter, such as the EnSite™ Array™ non-contact mapping catheter of St. Jude Medical, Inc. Catheter 120 is generally introduced to heart 122, vasculature, or ventricle 132 of patient 102 utilizing one or more introducers and using known procedures. Catheter 120 includes various bipole and unipole electrodes.

Figure 3A:
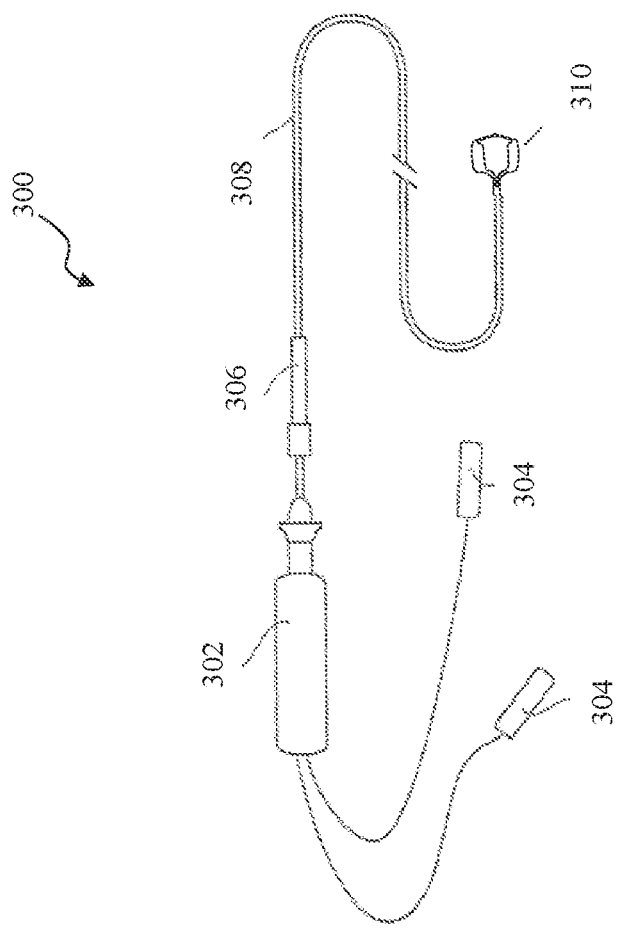
FIG. 3A is a schematic diagram of an exemplary catheter system for use in the system shown in FIG. 1 and FIG. 2.

FIG. 3A is a schematic diagram of an exemplary catheter system 300. Catheter system 300 includes a handle 302 and connectors 304 disposed proximal to handle 302 for making electrical connections to an electronic mapping system or other suitable computing system. Catheter system 300 includes an introducer sheath 306 located distal to handle 302 that a surgeon may use to deliver a sheath 308 into the body of patient 102. Sheath 308 extends from introducer sheath 306. Catheter system 300 further includes an electrode assembly 310 that protrudes from the distal end of sheath 308. Catheter system 300 may be embodied, for example, and without limitation, in catheter systems described in U.S. Pat. No. 8,224,416, assigned to St. Jude Medical Inc., which is hereby incorporated by reference herein.

Figure 3B:
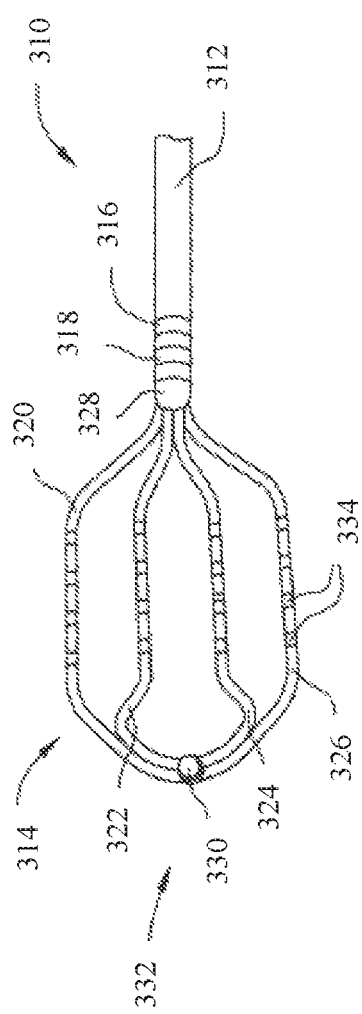
FIG. 3B is a schematic diagram of an exemplary electrode assembly for use in the catheter system shown in FIG. 3A.

FIG. 3B is a schematic diagram of an exemplary electrode assembly 310, for use in catheter system 300. Electrode assembly 310 includes a catheter body 312 coupled to a paddle 314. Catheter body 312 includes a first body electrode 316 and a second body electrode 318. Paddle 314 includes a first spline 320, a second spline 322, a third spline 324, and a fourth spline 326 coupled to catheter body 312 by a proximal coupler 328 and coupled to each other by a distal connector 330 at a distal end 332 of paddle 314. In one embodiment, first spline 320 and fourth spline 326 are one continuous segment and second spline 322 and third spline 324 are another continuous segment. In alternative embodiments, each of splines 320, 322, 324, and 326 are separate segments coupled to each other. Splines 320, 322, 324, and 326 include electrodes 334. Electrodes 334 may be embodied, for example, in ring electrodes evenly spaced along splines 320, 322, 324, and 326. In alternative embodiments, electrodes 334 may be embodied in point electrodes or any other suitable type of electrode.

Electrical activity produced by the heart manifests as small changes in charge of various cells of patient 102 that are detectable using specialized instrumentation, such as a data acquisition system (DAQ) 110 that is connected to surface ECG electrodes and the various electrodes of catheter 120. DAQ 110 includes various analog and digital circuits for sensing, conditioning, and relaying the electrogram signals generated at limb electrodes 104, precordial electrodes 106, and catheter electrodes to a computing system 112.

Computing system 112 includes a processor 114, an activation detection module 115, a memory 116, and a display 118. Computing system 112 may be embodied by the EnSite Precision™ system of St. Jude Medical, Inc., which is capable of measuring electrical activity of patient 102's heart to generate electrical activity maps that are produced using the apparatus and methods described herein. Such electrical activity maps, in certain embodiments, may not be generated within computing system 112. Computing system 112 may further be embodied by other ECG systems, such as, for example, the CARTO system of Biosense Webster, Inc., or the AURORA® system of Northern Digital Inc.

Computing system 112 is configured to receive multiple electrograms from DAQ 110 at processor 114 and control display 118 to present them on display 118 for viewing by a user, such as, for example, a physician, clinician, technician, or other user. Computing system 112 may further be configured to record the multiple electrograms in memory 116 and to provide the multiple electrograms to activation detection module 115. Activation detection module 115 is configured to process the multiple electrograms to determine an activation time for a given cardiac cycle. Such activation times are fundamental to producing electrical activity maps, such as the local activation time (LAT) map, the regular cycle length map, the voltage map, the conduction velocity map, and other products or diagnostic assessments. Activation detection module 115, in certain embodiments, includes one or more processors or processing devices programmed or otherwise configured according to the embodiments described herein to process electrogram signals to perform cardiac activation detection.

Figure 4:
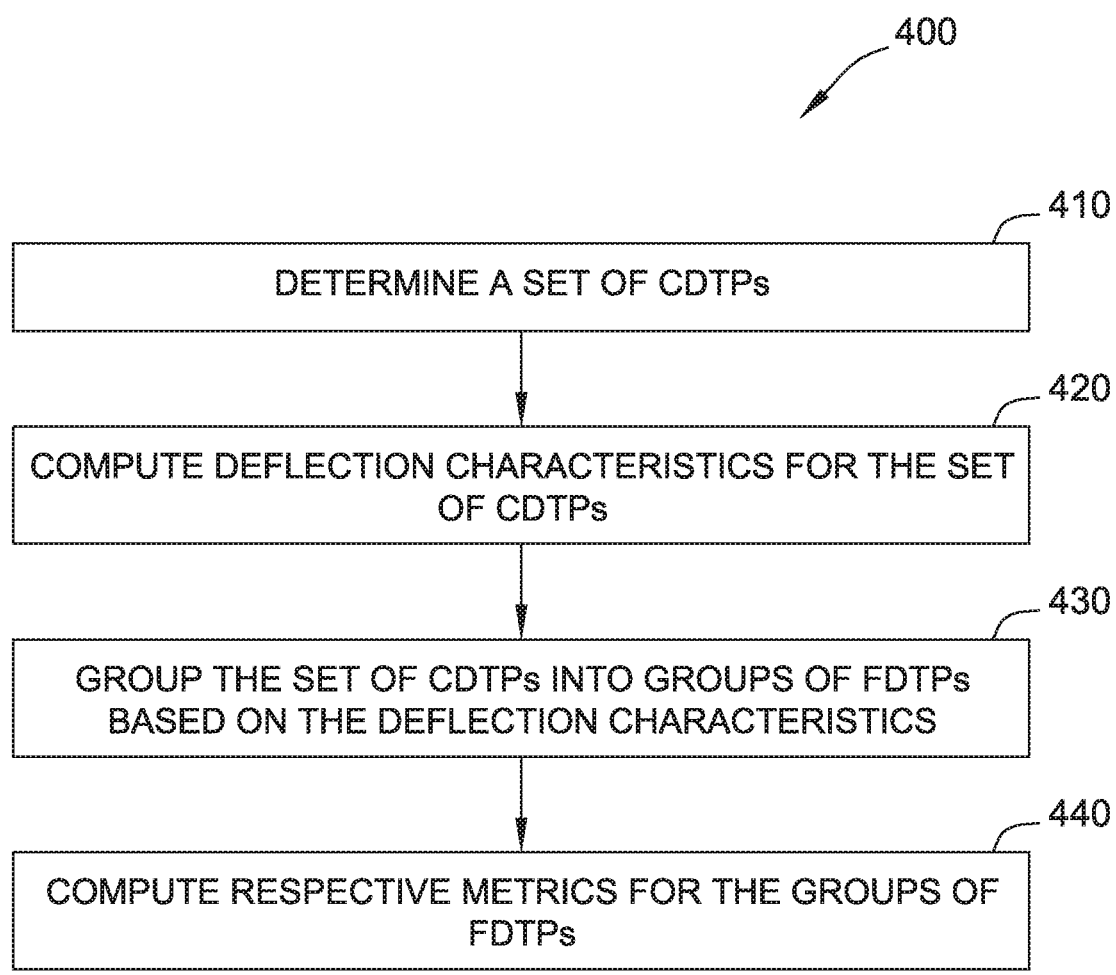
FIG. 4 is a flow diagram of an exemplary method of detecting cardiac activations of a patient.

FIG. 4 is a flow diagram of an exemplary method 400 of detecting cardiac activations of patient 102 based on one or more electrograms, including, for example, a surface ECG and multiple electrograms produced by multiple catheter electrodes placed in heart 122 of patient 102, detected by DAQ 110 and relayed to computing system 112. For a given electrogram i, activation detection module 115 computes an activation response based on the electrogram signal S(t) from which a set of CDTPs is determined 410.

According to embodiments of the systems and methods described herein, the activation response of a given electrogram i, may be computed using one of several computation methods, including, for example, and without limitation, a continuous wavelet transform method and a dv/dt method. In one embodiment, the dv/dt method is utilized to compute activation responses for electrograms, such as electrograms from bipole and/or unipole electrodes. In the dv/dt method, activation detection module 115 computes an activation response, $r_i(t)$, for bipole electrogram i according to the following:

$$r_i(t) = \left| \frac{dv}{dt} \right| \qquad \text{EQ. 1}$$

where, $$\frac{dv}{dt}$$

is a rust time derivative of Dipole electrogram i.

Similarly, in the dv/dt method, activation detection module 115 computes an activation response, $r_i(t)$, for unipole electrogram i according to the following:

$$r_1(t) = -\frac{dv}{dt} \qquad \text{EQ. 2}$$

where $$\frac{dv}{dt}$$

is a first time derivative or unipole electrogram i.

In certain embodiments, activation detection module 115 computes the activation response using the continuous wavelet transform (CWT) method. The CWT method produces a scalogram G (f,t), as a function of time, t, and frequency, f. Further, in the CWT method, an energy function L(t) is computed for the scalogram G(f,t). Signal noise present in the scalogram is removed by assigning values, G(f,t), below a predetermined noise threshold to zero. The activation response is then computed as the energy, L(t), according to the following:

$$r(t)=L(t)=\Sigma(f,t) \qquad \text{EQ. 3}$$

Activation detection module 115 determines 410 the set of CDTPs as local maximums within the activation response r(t). The set of CDTPs is referred to as $p_i$, where i=1, 2, . . . N, and where N is the number of CDTPs.

Activation detection module 115 then computes 420 deflection characteristics for the set of CDTPs. Deflection characteristics may include, for example, and without limitation, cycle length, peak-to-peak, local SNR, conduction velocity, voltage, and standard deviation of cycle length. For each CDTP, $p_i$, activation detection module 115 constructs M multi-dimension, i.e., d-dimensional, vectors, x, of deflection characteristics, sometimes referred to as "feature vectors." For N CDTPs, activation detection module 115 constructs N·M feature vectors. For a given CDTP, $p_i$, the feature vectors are defined as:

$$x_i^1, \ldots x_i^1 \in \mathbb{R} \qquad \text{EQ. 4}$$

In certain embodiments, computing 420 deflection characteristics includes, for example, computing a cycle length (CL) for each CDTP, $p_i$. In one embodiment, activation detection module 115 computes a $CL'_i$ and $CL''_i$ as follows:

$$CL'_i = \begin{cases} t_2 - t_1, & \text{if } i = 1 \\ t_i - t_{i-1}, & \text{else} \end{cases} \qquad \text{EQ. 5}$$

$$CL''_i = \begin{cases} t_3 - t_1, & \text{if } i = 1 \\ t_i - t_{i-2}, & \text{else} \end{cases} \qquad \text{EQ. 6}$$

where, $t_i$ denotes the time corresponding to CDTP $p_i$. Likewise, $t_{i-1}$ denotes the time corresponding to CDTP $p_{i-1}$. $CL'_i$ represents a CL between two sequential, in time, CDTPs, $p_{i-1}$ and $p_i$. $CL''_i$ represents a CL between a first CDTP, $p_{i-2}$, and two CDTPs later, $p_i$.

In certain embodiments, computing 420 deflection characteristics includes, for example, computing a peak-to-peak (PP) value for each deflection in the electrogram signal S(t). In one embodiment, activation detection module 115 computes, for each CDTP, $p_j$, a $PP_i$, within a time window, w, of, for example, plus or minus 10 milliseconds, exclusively, from the time, t, of CDTP $p_i$, as follows:

$$PP_i = \max_{|t-t_i|<w} S(t) - \min_{|t-t_i|<w} S(t) \qquad \text{EQ. 7}$$

In certain embodiments, computing 420 deflection characteristics includes, for example, computing a local SNR for each CDTP, which represents a strength of a given deflection relative to a baseline of the electrogram signal S(t). In one embodiment, to compute a local SNR for a CDTP $p_i$, activation detection module 115 computes a $SNR_{left}$, a $SNR_{center}$, and a $SNR_{right}$ as follows:

$$SNR_{left} = \sum_{|t-t_{left}|<w} r_i(t) \qquad \text{EQ. 8}$$

$$SNR_{center} = \sum_{|t-t_i|<w} r_i(t) \qquad \text{EQ. 9}$$

$$SNR_{left} = \sum_{|t-t_{right}|<w} r_i(t) \qquad \text{EQ. 10}$$

where, $t_{left}=t_i -60$ millesconds, $t_{right}=t_i+60$ millesconds, $r_i(t)$ is the activation response, and w is a time window set to, for example, 30 milliseconds. In alternative embodiments, computation of $SNR_{left}$ and $SNR_{right}$ may use time ranges other than 60 milliseconds. Similarly, in alternative embodiments, the time window w may be greater or smaller than 30 milliseconds. Activation detection module 115 computes the local SNR, $SNR_{local}$, as follows:

$$SNR_{local} = \frac{SNR_{center}}{SNR_{left} + SNR_{center} + SNR_{right}} \qquad \text{EQ. 11}$$

In certain embodiments, computing 420 deflection characteristics includes, for example, computing a conduction velocity (CV) vector, a voltage, a standard deviation of CL, or other deflection characteristic. Activation detection module 115 populates feature vectors as follows:

$$x_i^1 = [CL'_i, PP_i, SNR_{local}, CV] \qquad \text{EQ. 12}$$

$$x_i^2 = [CL''_i, PP_i, SNR_{local}, CV] \qquad \text{EQ. 13}$$

Activation detection module 115 then groups 430 the set of CDTPs into groups of FDTPs based on the deflection characteristics. Activation detection module 115 may use any suitable clustering methods or techniques, including, for example, a quick shift method as described in Comaniciu, Dorin, and Peter Meer, "Mean Shift: A Robust Approach Toward Feature Space Analysis," IEEE Transactions on Pattern Analysis and Machine Intelligence 24.5 (2002), pages 603-619, in Sheikh, Yaser Ajmal, Erum Arif Khan, and Takeo Kanade, "Mode-seeking by Medoidshifts," 2007 IEEE 11th International Conference on Computer Vision, IEEE, 2007, and in Vedaldi, Andrea, and Stefano Soatto, "Quick Shift and Kernel Methods for Mode Seeking," European Conference on Computer Vision, Springer Berlin Heidelberg, 2008, each of which is hereby incorporated by reference herein. Generally, activation detection module 115 clusters each element of the feature vectors into K groups, i.e., each $x_i^j$ is assigned to a group $c_i^j$, where $c=\{c_i^1, \ldots, c_i^M, \ldots, c_N^1, \ldots, c_N^M\}$, and $c_i^j \in \{1, 2, \ldots, K\}$. Accordingly, each CDTP can be assigned to one or more groups, and $c_i^j$ corresponds to a CDTP, $p_i$. Each group includes cardiac activations that are consistent with respect to each other in the group; such cardiac activations are referred to as FDTPs.

In one embodiment, activation detection module 115 groups 430 the CDTPs according to the following procedure:

1. Form the feature vectors $x_1^1, \ldots x_1^M, \ldots, x_N^1, \ldots x_N^M \in X = \mathbb{R}^d$, where $\mathbb{R}^d$ is a vector of real numbers having dimension d.
2. Estimate density p(x) with a Gaussian kernel having size h, $$\text{where } p(x) = \frac{1}{N \cdot M} \cdot \sum_{i=1}^{N \cdot M} g\left(\left\|\frac{x-x_i}{h}\right\|\right). \qquad \text{EQ. 14}$$

3. For each $x_i$, a quick shift method is used to determine $\pi(x_i)$ as the nearest neighbor for which there is an increment of the density p(x), where $$\pi(x_i) = \begin{cases} \operatorname{argmin}_{j:p(x_j)>p(x_i)} D_{i,j}, & \text{if } D_{i,j} = \|x_i - x_j\|_2 \\ i, & \text{if no neighbor larger than self} \end{cases} \qquad \text{EQ. 15}$$

4. Arrive at K groups from the quick shift result, such that each $x_i^j$ belongs to a group $c_i^j$, where $c=\{c_1^1, \ldots, c_N^M\}$, and $c_i^j \in \{1, 2, \ldots, K\}$, and such that each CDTP $p_i$ belongs to a group set $\{\cup_j c_i^j\}$.

In certain embodiments, the following exemplary quick shift algorithm may be employed in the above procedure.

```
For i = 1:NM
    j=i
    While(j!=π(x_j))
        j= π(x_j)
    end
    If there is a group having a center j
        append i to this group
    else
        create a new group with center j and append i to it
    end
End
```

Activation detection module 115 then computes 440 respective metrics for the groups of FDTPs. For example, a cycle length can be computed from the FDTPs in each group. Additionally, in certain embodiments of method 400, activation detection module 115 computes a dominant cycle length (DCL) map from groups of FDTPs that sufficiently span an observation window for the electrograms. For example, in one embodiment, the DCL map is computed from groups of FDTPs spanning at least 30% of the observation window. An exemplary procedure for computing a DCL is shown below, where there are N CDTPs.

If N=0, set DCL to 500 milliseconds.
If N=1, set DCL to 500 milliseconds.

If N=2, set the DCL to the time interval between CDTPs if the time interval is greater than 30% of the observation window and less than or equal to 500 milliseconds, otherwise set the DCL to 500 milliseconds.

If N=3, set the DCL to the minimum interval if the minimum interval is greater than 30% of the observation window and less than or equal to 500 milliseconds.

If N>=4, for each group k, compute a mean CL and a total CL based on the FDTPs, where $$CL_{mean} = \frac{\sum_{c_i=k} CL_i}{|FDTP_{s_k}|}, \text{ and } CL_{total} = \sum_{c_i=k} CL_i \qquad \text{EQ. 16}$$

Select a group having a smallest $CL_{mean}$ among groups having a $CL_{total}>30\%$ of the observation window, and set the DCL to the $CL_{mean}$, but no greater than 500 milliseconds, Else, when no group has a $CL_{total}>30\%$, select a group having a largest number of FDTPs and set the DCL to the $CL_{mean}$, but no greater than 500 milliseconds.

Figure 5:
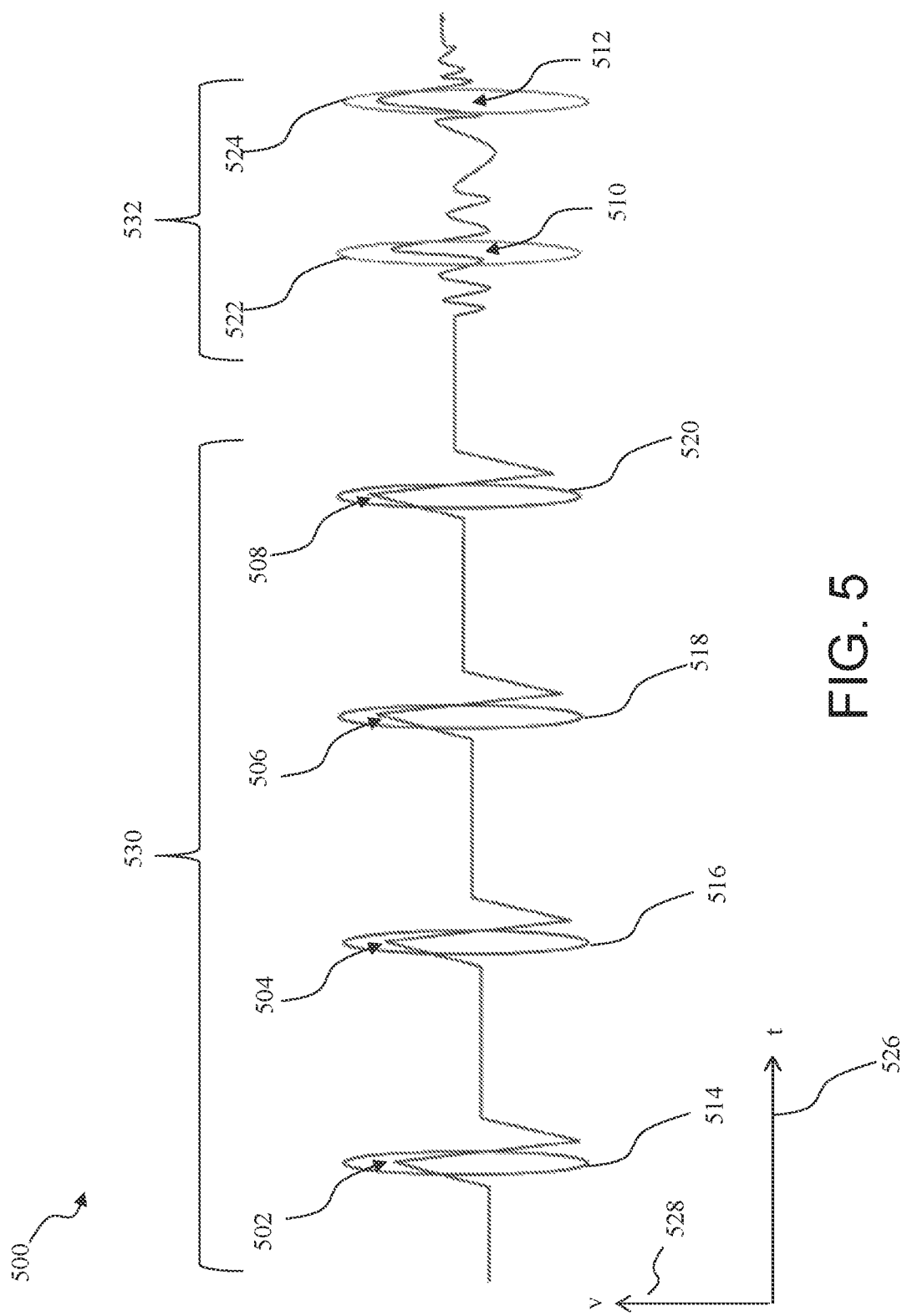
FIG. 5 is a graph of an exemplary electrogram having multiple deflections.

FIG. 5 is a graph of an exemplary electrogram 500 having multiple deflections 502, 504, 506, 508, 510, and 512 that are determined to be CDTPs 514, 516, 518, 520, 522, and 524, respectively. Electrogram 500 is plotted as voltage, v, versus time, t, where the horizontal axis 526 represents time and the vertical axis 528 represents voltage. Each of the CDTPs has an associated feature vector, including deflection characteristics, such as, for example, peak-to-peak and local SNR. Based on the feature vectors, CDTPs 514, 516, 518, and 520 are grouped into a first group 530 of FDTPs, and CDTPs 522 and 524 are grouped into a second group 532 of FDTPs. In certain embodiments of the systems and methods described herein, it is further determined that first group 530 is the dominant group and that second group 532 and, more specifically, CDTPs 522 and 524, are no longer considered for detecting cardiac activations.

Figure 6:
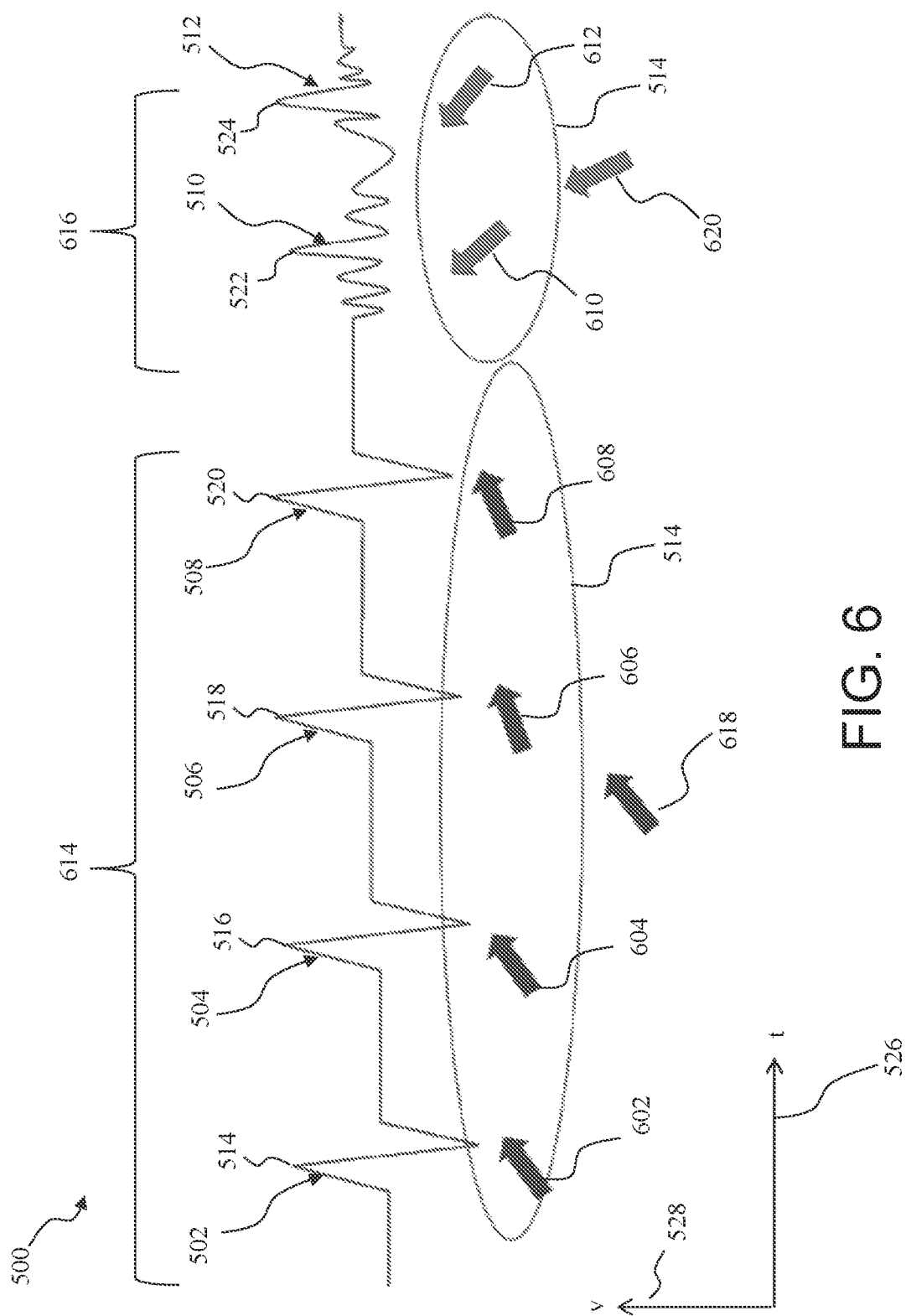
FIG. 6 is another graph of the electrogram shown in FIG. 5.

FIG. 6 is another graph of exemplary electrogram 500 having deflections 502, 504, 506, 508, 510, and 512, and CDTPs 514, 516, 518, 520, 522, and 524. As in FIG. 5, each CDTP is associated with a feature vector. However, in FIG. 6, each deflection is characterized by a conduction velocity 602, 604, 606, 608, 610, and 612. Based on the conduction velocities, the CDTPs 514, 516, 518, and 520 are grouped into a first group 614 of FDTPs, and CDTPs 522 and 524 are grouped into a second group 616 of FDTPs. A dominant conduction velocity is then computed for the first and second groups 614 and 616. First group 614 of FDTPs has a dominant conduction velocity 618. Second group 616 of FDTPs has a dominant conduction velocity 620.

The technical effects of the embodiments described above may include: (a) detecting cardiac activations based on similar deflection characteristics among groups of CDTPs; (b) improving cardiac activation detections in non-homogeneous electrograms; (c) improving cardiac activation detections over longer observation windows; (d) distinguishing among local cardiac activations and nearby cardiac electrical activity; (e) grouping CDTPs according to multiple deflection characteristics; (f) producing metrics based on CDTPs having common deflection characteristics.

Although certain embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

When introducing elements of the present disclosure or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As used herein, the terms "processor" and "computer" and related terms, e.g., "processing device", "computing device", and "controller" are not limited to just those integrated circuits referred to in the art as a computer, but broadly refers to a microcontroller, a microcomputer, a programmable logic controller (PLC), an application specific integrated circuit, and other programmable circuits, and these terms are used interchangeably herein. In the embodiments described herein, memory may include, but is not limited to, a computer-readable medium, such as a random access memory (RAM), and a computer-readable non-volatile medium, such as flash memory. Alternatively, a floppy disk, a compact disc-read only memory (CD-ROM), a magneto-optical disk (MOD), and/or a digital versatile disc (DVD) may also be used. Also, in the embodiments described herein, additional input channels may be, but are not limited to, computer peripherals associated with an operator interface such as a mouse and a keyboard. Alternatively, other computer peripherals may also be used that may include, for example, but not be limited to, a scanner. Furthermore, in the exemplary embodiment, additional output channels may include, but not be limited to, an operator interface monitor.

As various changes could be made in the above constructions without departing from the scope of the disclosure, it is intended that all matter contained in the above description or shown in the accompanying drawings shall be interpreted as illustrative and not in a limiting sense.

What is claimed is:

1. A system for detecting cardiac activations of a patient, the system comprising:
   a data acquisition system configured to detect an electrogram generated at an electrode disposed on or in the patient; and
   an activation detector communicatively coupled to the data acquisition system and configured to:
      receive the electrogram from the data acquisition system, the electrogram including electrogram signals;
      compute an activation response of the electrogram based on the electrogram signals, wherein the activation response indicates an activation time for a given cardiac cycle;

determine a set of candidate detection time points (CDTPs) in the activation response based on a predetermined criterion;
characterize each CDTP by assigning respective deflection characteristics for each CDTP of the set of CDTPs;
group CDTPs of the set of CDTPs having common deflection characteristics;
remove from the set of CDTPs at least one CDTP that cannot be grouped based on the respective deflection characteristics to determine a group of final detection time points (FDTPs) among the set of CDTPs having the common deflection characteristics; and
compute one or more metrics corresponding to the respective deflection characteristics based on the group of FDTPs having the common deflection characteristics, wherein the metrics include at least one of a cycle length computed as a length of time between two sequential, in time, FDTPs, a dominant cycle length map of the FDTPs, or a conduction velocity of the FDTPs.

2. The system of claim 1, wherein the activation detector is further configured to compute the activation response using a continuous wavelet transform of the electrogram signals that produces scalogram functions as functions of time and frequencies, the activation response is an energy as a function of time, and the energy is a sum of the scalogram functions over the frequencies.

3. The system of claim 1, wherein the data acquisition system is further configured to detect the electrogram from a bipole electrode disposed on a catheter disposed in the patient.

4. The system of claim 1, wherein the activation detector is further configured to compute a plurality of deflection characteristics for each CDTP of the set of CDTPs.

5. The system of claim 1, wherein the activation detector is further configured to compute a cycle length (CL) as a metric for each CDTP of the set of CDTPs in the FDTPs, wherein the cycle length is computed as a period of time between two sequential, in time, CDTPs.

6. The system of claim 5, wherein the activation detector is further configured to identify a group of FDTPs having similar cycle lengths.

7. The system of claim 6, wherein the activation detector is further configured to compute a dominant cycle length map from the group of FDTPs having similar cycle lengths and spanning an observation window above a predetermined threshold.

8. A method of detecting cardiac activations, said method comprising:
detecting an electrogram generated at an electrode disposed on or in a patient, the electrogram including electrogram signals;
computing an activation response of the electrogram based on the electrogram signals, wherein the activation response indicates an activation time for a given cardiac cycle;
determining a set of candidate detection time points (CDTPs) for the electrogram based on a predetermined criterion;
characterizing each CDTP by assigning respective deflection characteristics for each CDTP of the set of CDTPs;
grouping CDTPs of the set of CDTPs having common deflection characteristics;
removing from the set of CDTPs at least one CDTP that cannot be grouped based on the respective deflection characteristics to determine a group of final detection time points (FDTPs) among the set of CDTPs having the common deflection characteristics; and
computing one or more metrics corresponding to the respective deflection characteristics based on the group of FDTPs having the common deflection characteristics, wherein the metrics include at least one of a cycle length computed as a length of time between two sequential, in time, FDTPs, a dominant cycle length map of the FDTPs, or a conduction velocity of the FDTPs.

9. The method of claim 8, wherein computing the metrics further comprises computing a metric of a cycle length of each group of the FDTPs.

10. The method of claim 9, wherein computing the activation response comprises:
producing scalogram functions as functions of time and frequencies by applying a continuous wavelet transform on the electrogram signals; and
computing the activation response as a function of time by summing the scalogram functions over the frequencies.

11. The method of claim 8, wherein the set of CDTPs are local maximums of the activation response.

12. The method of claim 8, wherein computing the activation response comprises computing a derivative of voltage with respect to time (dv/dt) activation response.

13. The method of claim 8, wherein characterizing each CDTP further includes computing a cycle length, a peak-to-peak value, a local signal-to-noise ratio, and a conduction velocity, wherein the cycle length is computed as a period of time between two CDTPs.

14. The method of claim 13, wherein computing the cycle length comprises, for each CDTP in the set of CDTPs, computing a time difference between the CDTP and another CDTP in the set of CDTPs.

15. The method of claim 13, wherein computing the peak-to-peak value comprises, for a predetermined time window, computing a difference between a maximum of an activation response computed for the electrogram and a minimum of the activation response.

16. The method of claim 15, wherein grouping the set of CDTPs comprises grouping CDTPs, among the set of CDTPs, having a first peak-to-peak value into a first peak-to-peak group of FDTPs, and grouping CDTPs, among the set of CDTPs, having a second peak-to-peak value into a second peak-to-peak group of FDTPs.

17. The method of claim 13, wherein grouping the set of CDTPs into groups comprises grouping at least one CDTP of the set of CDTPs into a first group for cycle length and a second group for conduction velocity, or wherein computing respective metrics comprises computing a dominant cycle length map based on a group of FDTPs corresponding to the cycle length deflection characteristic.

18. The method of claim 8, wherein grouping the set of CDTPs into groups of FDTPs comprises:
forming feature vectors of the CDTPs, wherein a feature vector of each CDTP includes an array of deflection characteristics;
clustering the feature vectors into groups by employing a quick shift method on the feature vectors; and
assigning corresponding CDTPs in the groups of feature vectors to the groups of FDTPs.

19. The method of claim 18, wherein forming feature vectors further comprises forming the features vectors, wherein the feature vector of each CDTP includes an array of deflection characteristics having at least a cycle length, a peak-to-peak value, a local signal-to-noise ratio, and a conduction velocity.

20. The method of claim 8, wherein computing the metrics further comprises computing a metric of a conduction velocity of each group of FDTPs.

* * * * *